United States Patent
Bandekar et al.

(10) Patent No.: US 12,358,813 B2
(45) Date of Patent: Jul. 15, 2025

(54) KRAFT PULPING FOUL CONDENSATE TREATMENT PROCESS AND APPARATUS

(71) Applicant: NORAM ENGINEERING AND CONSTRUCTORS LTD., Vancouver (CA)

(72) Inventors: Rohan Bandekar, Vancouver (CA); James Theodore Wearing, Vancouver (CA); Jonathan Edward Foan, Vancouver (CA)

(73) Assignee: NORAM ENGINEERING AND CONSTRUCTORS LTD., Vancouver (CA)

( * ) Notice: Subject to any disclaimer, the term of this patent is extended or adjusted under 35 U.S.C. 154(b) by 902 days.

(21) Appl. No.: 17/593,348

(22) PCT Filed: Mar. 17, 2020

(86) PCT No.: PCT/CA2020/050355
§ 371 (c)(1),
(2) Date: Sep. 16, 2021

(87) PCT Pub. No.: WO2020/186350
PCT Pub. Date: Sep. 24, 2020

(65) Prior Publication Data
US 2022/0185700 A1 Jun. 16, 2022

Related U.S. Application Data

(60) Provisional application No. 62/820,182, filed on Mar. 18, 2019.

(51) Int. Cl.
*B01D 3/34* (2006.01)
*C02F 1/20* (2023.01)
*C02F 1/66* (2023.01)
*C02F 101/16* (2006.01)
*C02F 101/34* (2006.01)
*C07C 29/74* (2006.01)
*D21C 11/00* (2006.01)
(Continued)

(52) U.S. Cl.
CPC .............. *C02F 1/20* (2013.01); *B01D 3/346* (2013.01); *C02F 1/66* (2013.01); *C07C 29/74* (2013.01);
(Continued)

(58) Field of Classification Search
CPC ...... B01D 3/346; C02F 1/20; C02F 2101/322; C02F 2103/28; D21C 11/0007
See application file for complete search history.

(56) References Cited

U.S. PATENT DOCUMENTS

| 8,440,159 B2 | 5/2013 | Brucher et al. |
| 9,320,986 B2 | 4/2016 | Der et al. |
| 2018/0117525 A1 | 5/2018 | Davis et al. |

FOREIGN PATENT DOCUMENTS

| CA | 1088957 | 11/2004 |
| CA | 2751602 A1 | 8/2010 |

(Continued)

OTHER PUBLICATIONS

Lin, B. (2007) "The Basics of Foul Condensate Stripping," Tappi Kraft Recovery Course.
(Continued)

*Primary Examiner* — Bradley R Spies
(74) *Attorney, Agent, or Firm* — David J. McGruder; Oyen Wiggs Green & Mutala LLP (57) ABSTRACT

Processes and systems for treating Kraft pulping foul condensate are provided. The processes comprise removing volatile compounds from the foul condensate to produce a resulting condensate and removing methanol from the resulting condensate. The systems comprise a volatile compound removal stage and a methanol removal stage downstream of and in fluid communication with the volatile removal stage.

9 Claims, 4 Drawing Sheets

(51) Int. Cl.
*D21C 11/08* (2006.01)
*C02F 101/32* (2006.01)
*C02F 103/28* (2006.01)

(52) U.S. Cl.
CPC .......... *D21C 11/0007* (2013.01); *D21C 11/08* (2013.01); *C02F 2101/16* (2013.01); *C02F 2101/322* (2013.01); *C02F 2101/34* (2013.01); *C02F 2103/28* (2013.01)

(56) References Cited

FOREIGN PATENT DOCUMENTS

| | | | |
|---|---|---|---|
| CA | 2815166 | A1 | 4/2012 |
| CA | 2916012 | C | 12/2014 |
| EP | 1424435 | A2 | 6/2004 |
| WO | WO-9937853 A1 * | 7/1999 | ............. D21C 11/06 |
| WO | 2009/070110 | | 6/2009 |
| WO | 2014201555 | A1 | 12/2014 |

OTHER PUBLICATIONS

Emilsson, K. et al., "Extended Stripping and Usage of Evaporator Condensates at Värö Mill", Sweden. Tappi, 1997, Minimum Effluent Mills Symposium, 191.

Niemela, K., "Sulfur and Nitrogen Compounds in Rectified Methanol from Foul Condensate Stripping", PAPTAC/TAPPI International Chemical Recovery Conference Proceedings, Charleston, South Carolina, Jun. 6-11, 2004.

* cited by examiner

KRAFT PULPING FOUL CONDENSATE TREATMENT PROCESS AND APPARATUS

CROSS-REFERENCE TO RELATED APPLICATIONS

This application claims priority from U.S. application No. 62/820,182 filed 18 Mar. 2019. For the purposes of the United States, this application claims the benefit under 35 U.S.C. § 119 of U.S. application No. 62/820,182 filed 18 Mar. 2019 and entitled KRAFT PULPING FOUL CONDENSATE TREATMENT PROCESS AND APPARATUS which is hereby incorporated herein by reference for all purposes.

TECHNICAL FIELD

The present invention relates to processes and systems for treating Kraft pulping foul condensate to yield a stripped condensate suitable for re-use in the Kraft pulping process. The recovered methanol may be used as a substitute for merchant methanol in Kraft pulping processes. NOx formation may be reduced or eliminated.

BACKGROUND

In the Kraft pulping process, multiple-effect evaporators are used to concentrate spent cooking liquor, referred to as black liquor, to allow for the combustion of the concentrated black liquor and consequent recovery of its thermal and chemical values. Condensates are produced from each of the typically 4-8 effects in the evaporator line. The evaporator effects to which the black liquor is first introduced produce condensates with the highest concentration of contaminants. Lower concentrations of contaminants are found in each subsequent effect. The condensates from these subsequent effects are typically clean enough that the condensate may be re-used as a source of washing or dilution water in the Kraft pulping process. However, the contaminants in the condensate from effects where black liquor is first introduced, referred to as foul condensate, are highly contaminated and must be purified prior to re-use in the Kraft pulping process. If there is a significant carryover of black liquor due to foaming or liquid entrainment in the evaporator, these contaminants may include some non-volatile compounds. These non-volatile contaminants are usually minimized through careful design of evaporation equipment. The presence of volatile contaminants in the condensates cannot be avoided because they are removed along with the water vapour in the evaporation process due to their volatility. Typically, a Kraft pulp mill will employ a stripper column in which the volatile materials are stripped from the condensate using steam or, more rarely, using air, prior to reuse in the mill or routing to effluent treatment.

Whereas ideally, it would be desired to utilize the condensates in the Kraft pulp bleaching process, in practice, this is rarely achievable because the residual levels of contaminants are too high and interfere with pulp quality or bleaching efficiency. For example, lignin removal and brightness gain in bleaching are impaired by the presence of residual sulfur compounds. Thus, very high efficiency would need to be achieved in the foul condensate treatment process to allow re-use of condensates in bleaching.

A list of contaminants measured in a foul condensate from evaporation of Kraft softwood pulp mill black liquor is shown in Table 1. These include reduced sulfur compounds that impart a foul odour to the condensates, terpenes and terpene alcohols (principle components of turpentine), ammonia, ketones, aldehydes and alcohols. By far, the largest constituent is an alcohol, methanol. Various contaminants are soluble in methanol and form azeotropic mixtures with methanol. This makes it very difficult to recover methanol from the foul condensate that is not contaminated.

TABLE 1

Typical Concentrations of Contaminants in a Softwood Foul Condensate

| Constituent | g/L | Constituent | g/L |
| --- | --- | --- | --- |
| Methanol | 11.1 | Methyl mercaptan | 0.373 |
| Ethanol | 0.516 | Acetone | 0.056 |
| Ammonia | 0.417 | Methyl Ethyl Ketone | 0.049 |
| Hydrogen Sulfide | 0.434 | Acetaldehyde | 0.05 |
| Dimethyl Sulfide | 0.654 | Terpinols | 0.15 |
| Dimethyl Disulfide | 0.15 | Pinenes | 0.133 |

A number of processes and systems exist to treat foul condensate, such as:

Emillson et al. Extended Stripping and Usage of Evaporator Condensates at Värö Mill, Sweden. Tappi, 1997, Minimum Effluent Mills Symposium, 191;

International Application No. WO 99/37853;

European Patent No. EP 1 424 435;

U.S. Pat. No. 8,440,159;

U.S. Pat. No. 9,320,986;

Canadian Patent No. 2916012.

Treatment of foul condensate from Kraft pulping processes for re-use is difficult from the process engineering point of view for one or more of the following reasons:
  (a) Existing technologies leave considerable amounts of volatile contaminants in the stripped condensate such that its use in the bleach plant is precluded.
  (b) Existing technologies transfer ammonia to the concentrated non-condensable gas (CNCG) stream which is burned in a recovery boiler, lime kiln, or dedicated incinerator resulting in nitrogen oxides (NOx) emissions from the Kraft mill.
  (c) Existing technologies recover methanol that is too contaminated to use in place of merchant methanol in Kraft pulping processes. Merchant methanol is purchased by most Kraft pulp mills for use as a reducing agent in chloride dioxide generators. The reactions in the generators are very sensitive to the presence of contaminants such as terpenes, terpenols, sulfur compounds, etc., which can produce localized decompositions in the generator, reducing efficiency and throughput.

There is a general desire for simple and cost effective Kraft pulping foul condensate treatment processes and systems for producing a stripped condensate with minimal volatile contaminants for re-use in the Kraft pulping process while minimizing NOx formation and producing methanol with minimal contaminants that can be used as a substitute for merchant methanol in Kraft pulping processes.

The foregoing examples of the related art and limitations related thereto are intended to be illustrative and not exclusive. Other limitations of the related art will become apparent to those of skill in the art upon a reading of the specification and a study of the drawings.

SUMMARY

The present technology relates to processes and systems for treating foul condensates. A process according to an example of the present technology comprises the steps of:

(a) removing volatile compounds from the foul condensate to produce a resulting condensate; and
(b) removing methanol from the resulting condensate.

In some embodiments the volatile compounds are removed by:
an air stripper; and/or
a first steam stripper.

In some embodiments the methanol is removed by a second steam stripper.

In some embodiments the process comprises reducing or eliminating nitrogen oxides (NOx) emissions by removing ammonia from the foul condensate. The ammonia may be removed, for example by adding an acid to the foul condensate. The acid may optionally be added to the foul condensate in a feed tank and/or an ammonia scrubber. The acid may, for example comprise an inorganic acid an inorganic acid salt, an organic acid or an organic acid salt. In an example embodiment the acid comprises: sulphuric acid or sodium bisulphite.

In some embodiments an air stripper maintains the temperature of the foul condensate below about 90° C. or about 80° C. or about 70° C. or about 60° C. For example, the air stripper may maintain the temperature of the foul condensate between about 50° C. and about 60° C.

In some embodiments a mass of oxygen-containing gas used to strip the foul condensate in an air stripper is controlled to maintain the oxygen-containing gas below its Lower Explosive Limit (LEL). In some embodiments a mass of oxygen-containing gas used to strip the foul condensate in an air stripper is less than about 10% by weight (wt. %) of the mass of the foul condensate supplied to the air stripper. In some embodiments a mass of oxygen-containing gas used to strip the foul condensate in an air stripper is less than about 5% by weight (wt. %) of the mass of the foul condensate supplied to the air stripper.

In some embodiments a first steam stripper used to remove the volatile compounds maintains the temperature of the foul condensate below about 100° C. or about 90° C.

In some embodiments a mass of steam used to strip the foul condensate in the first steam stripper is less than about 10% by weight (wt. %) or less than about 5% by weight of the mass of the foul condensate supplied to the first steam stripper.

In some embodiments a second steam stripper used to remove the methanol maintains the temperature of the foul condensate above about 100° C. For example, the second steam stripper may maintain the temperature of the foul condensate between about 100° C. and about 120° C.

In some embodiments a mass of steam used to strip the foul condensate in the second steam stripper is greater than about 10% by weight (wt. %) or about 20% by weight of the mass of the foul condensate supplied to the second steam stripper In some embodiments a vapour pressure of the volatile compounds is greater than the vapour pressure of the methanol at a given temperature.

In some embodiments wherein the methanol can be or is used as a substitute for merchant methanol in Kraft pulping processes.

In some embodiments which use an air stripper to remove the volatile compounds the air stripper comprises a packed column, a tray column, a fluidized-bed column, or a froth column.

In some embodiments which use first steam stripper to remove the volatile compounds the first steam stripper comprises a packed column, a tray column, a fluidized-bed column, or a froth column.

In some embodiments where a second steam stripper is used to remove the methanol the second stream stripper comprises a packed column, a tray column, a fluidized-bed column, or a froth column.

In some embodiments process comprises purifying the methanol. For example, purifying the methanol may comprise one or more of condensing, decanting, reverse osmosis, and treating the methanol with activated carbon.

In some embodiments where an air stripper is used to remove the volatile compounds the process comprises venting the air stripper to a Kraft mill's dilute non-condensable gas (DNCG) system.

In some embodiments the process comprises venting the foul condensate to a Kraft mill's concentrated non-condensable gas (CNCG) system.

In some embodiments which use a first steam stripper to remove the volatile compounds the process comprises venting the first steam stripper to a Kraft mill's CNCG system.

In some embodiments which use a second steam stripper to remove the methanol the process comprises venting the second steam stripper to a Kraft mill's CNCG system.

Another aspect of the present technology provides a foul condensate treatment system. The system has example application in a Kraft pulp mill. The system comprises:
(a) a volatile compound removal stage; and
(b) a methanol removal stage downstream of and in fluid communication with the volatile compound removal stage.

In some embodiments the volatile compound removal stage comprises an air stripper. In some embodiments the volatile compound removal stage comprises a first steam stripper.

In some embodiments the methanol removal stage comprises a second steam stripper (such embodiments do not necessarily need to have a first steam stripper but could have a first steam stripper).

Some embodiments further comprise a nitrogen oxides (NOx) emissions elimination stage. The NOx emissions elimination stage may, for example comprise an acid storage tank connected to and in fluid communication with the foul condensate. For example the acid storage tank may be connected to and in fluid communication with a foul condensate feed tank and/or connected to and in fluid communication with an ammonia scrubber. The ammonia scrubber, where present, may be downstream, connected to, and in fluid communication with the volatile compounds removal stage.

In some embodiments which include an air stripper the air stripper comprises a packed column, a tray column, a fluidized-bed column, or a froth column.

In some embodiments which include a first steam stripper the first steam stripper comprises a packed column, a tray column, a fluidized-bed column, or a froth column.

In some embodiments which include a second steam stripper the second stream stripper comprises a packed column, a tray column, a fluidized-bed column, or a froth column.

Some embodiments comprise a methanol purification stage. The methanol purification stage may, for example comprise one or more of a condenser, decanter, reverse osmosis membrane, and activated carbon.

In some embodiments the system further comprises a Kraft mill DNCG system connected to and in fluid communication with the volatile compounds removal stage.

In some embodiments the system further comprises a Kraft mill CNCG system connected to and in fluid communication the volatile compounds removal stage.

In some embodiments the system further comprises a Kraft mill CNCG system connected to and in fluid communication the methanol removal stage.

Further aspects and example embodiments are illustrated in the accompanying drawings and/or described in the following description.

It is emphasized that the invention relates to all combinations of the above features, even if these are recited in different claims.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Unless context dictates otherwise, the term "foul condensate" (as used herein) refers to concentrated spent cooking liquor from Kraft pulping processes. Foul condensate typically comprises volatile and/or non-volatile contaminants that must be removed before the condensate can be re-used in the Kraft pulping process. Foul condensate contaminants include, but are not limited to, methanol, ethanol, ammonia, hydrogen sulphide, dimethyl sulphide, dimethyl disulphide methyl mercaptan, acetone methyl ethyl ketone, acetaldehyde terpinols, pinene, turpentine, turpenes, and turpene alcohols. The composition of foul condensate will differ depending on the Kraft pulping process conditions and the type of wood processed by the Kraft mill. For example, the concentration of turpenes is typically greater in foul condensate produced by a softwood Kraft pulp mill than a hardwood Kraft pulp mill.

Unless context dictates otherwise, the term "Kraft pulping" (as used herein) refers to a process for conversion of wood into wood pulp (i.e. cellulose fibers).

Unless context dictates otherwise, the term "nitrogen oxides" (NOx) (as used herein) means nitrogen oxide (NO), nitrogen dioxide ($NO_2$), and other oxides of nitrogen.

Unless context dictates otherwise, the term "volatile compounds" (as used herein) refers to compounds contained in foul condensate from Kraft pulping processes that have a higher vapour pressure than methanol at a given temperature. Volatile compounds that contain sulphur include (but are not limited to) hydrogen sulphide ($H_2S$), methyl mercaptan, dimethyl sulphide, and terpenes. Other volatile compounds that do not contain sulphur include (but are not limited to) acetone, acetaldehyde, and pinene.

Unless context dictates otherwise, the term "Lower Explosive Limit" (LEL) (as used herein) refers to the minimum concentration of a gas and/or vapour that will burn in air. Unless context dictates otherwise, the term "Upper Explosive Limit" (UEL) (as used herein) refers to the maximum concentration of a gas and/or vapour that will burn in air. Above the UEL, the gas and/or vapour is too "rich" to burn. The range between the LEL and the UEL is known as the flammable range for that gas and/or vapour.

Unless context dictates otherwise, the term "concentrated non-condensable gas" (CNCG) (as used herein) refers to a concentrated gas stream that is unable to condense at a temperature above about 30° C. and that contains flammable compounds at a concentration above corresponding Lower Explosive Limits.

Unless context dictates otherwise, the term "dilute non-condensable gas" (DNCG) (as used herein) refers to a dilute gas stream that is unable to condense at a temperature above about 30° C. and contains no flammable compounds at a concentration above corresponding Lower Explosive Limits.

Unless context dictates otherwise, the term "about" (as used herein) means near the stated value (i.e. within ±5% of the stated value).

Some example embodiments of the present invention provide processes and systems for treating foul condensate to achieve one or more of the following advantages: (1) yield a stripped condensate suitable for re-use in the Kraft pulping process; (2) reduce or eliminate NOx formation; and (3) produce methanol suitable for use as a substitute for merchant methanol in Kraft pulping processes.

Figure 1:
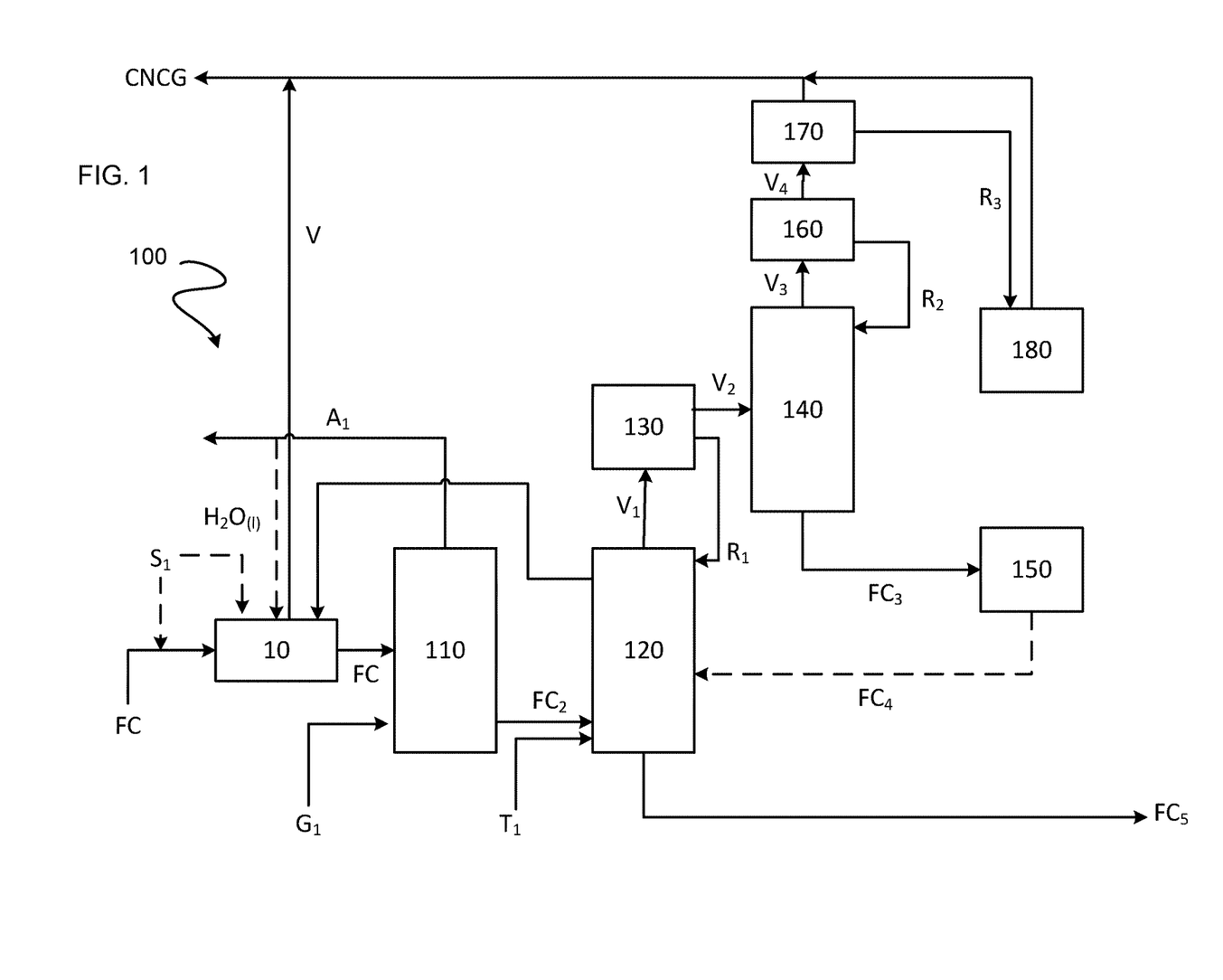
FIG. 1 is a schematic illustration of a foul condensate treatment process according to an example embodiment of the present invention.

A foul condensate treatment process (FCTP) 100 in accordance with an example embodiment is schematically illustrated in FIG. 1. Foul condensate FC from Kraft pulping is sequentially treated to yield a stripped condensate suitable for re-use in the Kraft pulping process. In some embodiments, FCTP 100 reduces or eliminates NOx formation and/or produces methanol suitable for use as a substitute for merchant methanol in Kraft pulping processes. FCTP 100 comprises an air stripper 110. Air stripper 110 is a device that brings foul condensate FC into contact with a flow of gas into which volatile compounds may evaporate from the liquid foul condensate FC. Air stripper 110 may be constructed to provide an interface between liquid foul condensate FC and the gas to provide a sufficiently large surface area for the volatile compounds to enter the gas phase. For example, air stripper 110 may comprise a packed column, a tray column, a fluidized-bed column, or a froth column. In some embodiments, air stripper 110 comprises a packed tower such as a mass transfer column. The column may have structured, fixed, or loose packing as is conventionally known. In some embodiments, air stripper 110 comprises a fluidized bed stripper. The fluidized bed air strippers are commercially available from sources such as Fluid Technologies (Environmental) Ltd. of Kingston-upon-Thames, UK. One example fluidized bed air stripper is disclosed in US Patent Application Publication No. 2018/0117525A1, which is hereby incorporated herein by reference for all purposes). A fluidized bed stripper comprises a column of fluidized eccentric spheres of plastic which create a high surface area for mass transfer.

When air stripper 110 is operating, volatile compounds from foul condensate FC evaporate into spent stripping gas $A_1$ and are thereby separated from foul condensate FC. Foul condensate FC stored in a feed tank 10 is supplied to air stripper 110. A gas $G_1$ is supplied to air stripper 110. In some embodiments, gas $G_1$ comprises air or another oxygen-containing gas. In some embodiments, gas $G_1$ comprises an inert gas (e.g. nitrogen, argon, etc.). A high capacity blower (not shown) forces ambient or heated gas $G_1$ into the bottom of air stripper 110 where gas $G_1$ is brought into contact with foul condensate FC to separate the volatile compounds from the liquid foul condensate FC. In some embodiments, foul condensate FC is heated before introduction into air stripper 110. In some embodiments, vapour V from foul condensate FC in feed tank 10 is directed to the Kraft mill's concentrated non-condensable gas (CNCG) stream to reduce the pressure inside tank 10. In some embodiments, some volatile compounds from tank 10 are directed to the CNCG stream in vapour V. The CNCG stream may be burned in a recovery boiler and/or in a lime kiln and/or in a dedicated incinerator.

It is desirable to maintain conditions in air stripper 110 that reduce volatilization of methanol while ensuring that the volatile compounds are stripped adequately from foul condensate FC. Accordingly, the temperature and column height of air stripper 110 may be adjusted to optimize this differential removal.

Air stripper 110 maintains the temperature of foul condensate FC below about 100° C. In some embodiments, air stripper 110 maintains the temperature of foul condensate FC below about 90° C. In some embodiments, air stripper 110 maintains the temperature of foul condensate FC below about 80° C. In some embodiments, air stripper 110 maintains the temperature of foul condensate FC below about 70° C. In some embodiments, air stripper 110 maintains the temperature of foul condensate FC below about 60° C. In some embodiments, air stripper 110 maintains the temperature of foul condensate FC between about 50° C. and about 90° C. In some embodiments, air stripper 110 maintains the temperature of foul condensate FC between about 50° C. and about 80° C. In some embodiments, air stripper 110 maintains the temperature of foul condensate FC between about 50° C. and about 70° C. In some embodiments, air stripper 110 maintains the temperature of foul condensate FC between about 50° C. and about 60° C.

The mass of gas $G_1$ used to strip foul condensate FC is less than about 10% by weight (wt. %) of the mass of foul condensate FC supplied to air stripper 110. In some embodiments, the mass of gas $G_1$ is less than about 5 wt. % of the mass of foul condensate FC supplied to air stripper 110. Process conditions may be adjusted in air stripper 110 to achieve a desired efficiency for removing volatile compounds.

The ratio of gas-to-liquid flow through air stripper 110 controls the removal rate of volatile compounds. While an increase in this ratio generally results in greater removal rates, blower operation costs are higher. The height of air stripper 110 also affects removal efficiency. An optimum balance between the gas-to-liquid ratio and the stripper height results in acceptable removal efficiencies at the lowest combination of capital and operational cost.

The flow rate of foul condensate FC through air stripper 110 determines the diameter of air stripper 110. The type of packing material and the surface area of the packing will affect the mass transfer rate and/or gas pressure drop through the stripper. Smaller diameter packing material offers more surface area than larger diameter materials, but also provides greater resistance to gas flow. The ratio of column diameter to packing size should be selected to prevent channeling of foul condensate FC along the walls of air stripper 110. In some embodiments, the packing material is manufactured from one or more of polypropylene, PVC, and ceramic.

Spent stripping gas $A_1$ is cooled to condense water vapour and is then directed to the Kraft mill's dilute non-condensable gas (DNCG) system for combustion in a recovery boiler and/or separate incinerator. The flow rate of gas $G_1$ is monitored to ensure that the concentration of volatiles in spent stripping gas $A_1$ is less than a Lower Explosive Limit (LEL). Condensed water vapour $H_2O_{(l)}$ is returned to feed tank 10.

In addition to volatile sulphur-containing compounds, ammonia is an inorganic compound that may be present in foul condensate FC. Ammonia exists in foul condensate FC both in the dissolved gas form ($NH_{3(g)}$) and in true solution as ammonium ions ($NH_4^+{}_{(aq)}$). These two nitrogen species are present in a dynamic equilibrium according to the equation:

$$NH_{3(g)} + FC_{(l)} \leftrightarrow NH_4^+{}_{(aq)} + OH^-{}_{(aq)}$$

The relative concentration of these two nitrogen species depends on the pH of foul condensate FC and temperature. In general, at a temperature of 20° C. and a pH of 7 or below, essentially only ammonium ions are present. As the pH increases above 7, the chemical equilibrium is gradually shifted to the left in favor of ammonia gas formation.

If NOx control is required, an acid $S_1$ may be added to foul condensate FC to convert ammonia to non-volatile ammonium ions. For example, enough acid $S_1$ may be added such that the pH of foul condensate FC delivered into air stripper 110 has a pH of about 7 or lower. The ammonium ions exit air stripper 110 with the resulting concentrate $FC_2$. In the example embodiment illustrated in FIG. 1, acid $S_1$ is added to foul condensate FC prior to its introduction into air stripper 110. For example, acid $S_1$ may be added to feed tank 10 or to foul condensate FC prior to storage in feed tank 10. In some embodiments, acid $S_1$ comprises sulphuric acid and/or sodium bisulphite. The ammonium ions associate with sulphate anions in solution. Other organic and/or inorganic acids and/or acid salts may be used to convert ammonia to ammonium ions.

In some embodiments, ammonia is scrubbed from the overhead gas of air stripper 110 using acid $S_1$. Recovered ammonium ions may be directed to the resulting concentrate $FC_2$. For example, in the embodiment illustrated in FIG. 2, a FCTP 200 is schematically illustrated. FCTP 200 comprises a stripper 210 for removing ammonia and volatile compounds. Many features and components of FCTP 200 are similar to features and components of FCTP 100, with the same reference numerals being used to indicate features and components that are similar between the embodiments. Stripper 210 comprises air stripper 110 and an ammonia scrubber 212 for scrubbing ammonia from overhead gas using acid $S_1$. Recovered ammonium $NH_4^+$ may be directed to Kraft mill effluent treatment. Ammonium may beneficial in Kraft mill effluent as a nutrient in biological treatment. In some embodiments, ammonia is recovered as ammonium sulphate (($NH_4$)$_2SO_{4(l)}$, which may be directed to Kraft mill effluent treatment. In the illustrated embodiment, stripper 210 forms a single device comprising air stripper 110 and ammonia scrubber 212. Persons skilled in the art will recognize that air stripper 110 and ammonia scrubber 212 may be separate devices.

Figure 2:
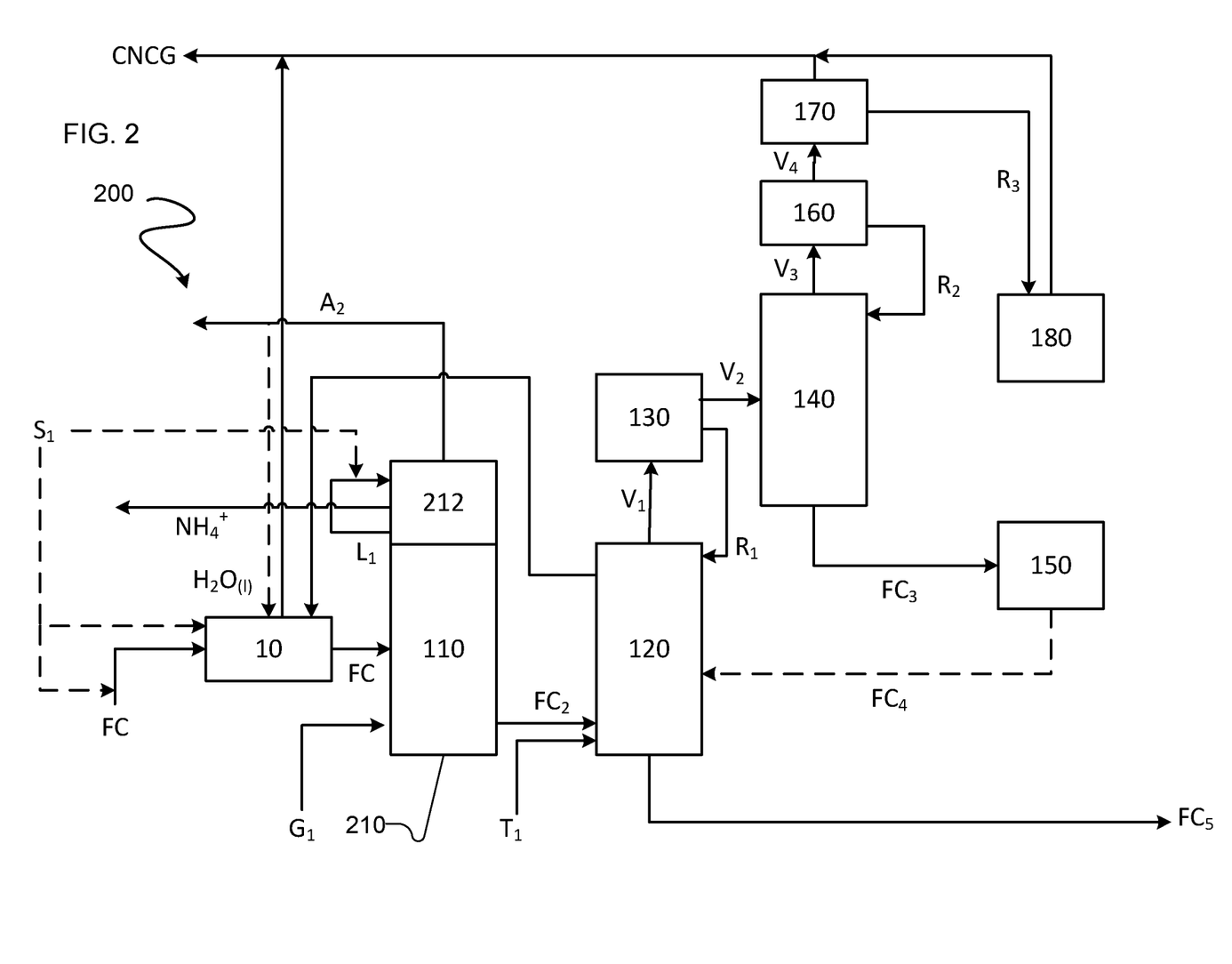
FIG. 2 is a schematic illustration of a foul condensate treatment process according to an example embodiment of the present invention.

Spent stripping gas $A_2$ is cooled to condense water vapour and is then directed to the Kraft mill's dilute non-condensable gas (DNCG) system for combustion in a recovery boiler and/or separate incinerator. Gas flow is monitored to ensure that spent stripping gas $A_2$ is diluted below a Lower Explosive Limit (LEL). Condensed water vapour $H_2O_{(l)}$ is returned to feed tank 10. In some embodiments, a liquid $L_1$ collected from air stripper 210 is redirected to the top of air stripper 210. Acid $S_1$ may be added to liquid $L_1$ and the mixture used to contact rising gas flow through air stripper 110 to scrub ammonia.

Since higher temperatures and/or a higher gas/liquid ratio is required to remove methanol from foul condensate FC, air stripper 110 effectively removes volatile compounds while retaining a large percentage of the methanol in the resulting condensate $FC_2$. Methanol is subsequently concentrated and purified by FCTP 100 in a second separation stage (e.g. steam stripper 120). Following treatment in air stripper 110, the concentration of volatile compounds in condensate $FC_2$ is reduced. Accordingly, the volatile compounds are not available in such high concentrations to interact and form less volatile contaminants that are more difficult to separate from foul condensate FC. In some embodiments, the volatile compounds are not available in such high concentrations to complicate methanol purification by solubilizing in methanol in air stripper 110 to form distillation azeotropes. The methanol produced by FCTP 100 and 200 thus has minimal contaminants and may be used as a substitute for merchant methanol in Kraft pulping processes.

Condensate $FC_2$ is collected from air stripper 110 and is optionally pre-heated (not shown) and directed to second separation stage. In some embodiments, second separation stage comprises a steam stripper 120. Condensate $FC_2$ may be directed to a mid-point of the steam stripper column. In some embodiments, steam stripper 120 comprises a packed column, a tray column, a fluidized-bed column, or a froth column. In some embodiments, steam stripper 120 comprises a packed tower such as a mass transfer column. The column may have structured, fixed, or loose packing as is conventionally known. Steam stripper 120 is provided with multiple vapour and/or liquid equilibrium stages using trays and/or continuous packing at a mid-point in the column. Steam $T_1$ is introduced into the bottom of steam stripper 120 to vaporize methanol together with some remaining volatile compounds and water present in condensate $FC_2$. In some embodiments, steam $T_1$ comprises steam from a boiler and/or from one or more of the evaporator effects of the Kraft pulping. In some other embodiments, steam $T_1$ may be produced in a re-boiler installed at a bottom end of steam stripper 120.

Steam stripper 120 heats condensate $FC_2$ to a temperature of at least about 100° C. In some embodiments, steam stripper 120 maintains the temperature of condensate $FC_2$ between about 100° C. and about 120° C.

In some embodiments, the mass of steam $T_1$ used to strip condensate $FC_2$ is greater than about 10 wt. % of the mass of condensate $FC_2$ supplied to steam stripper 120. In some embodiments, the mass of steam $T_1$ is greater than about 20 wt. % of the mass of condensate $FC_2$ supplied to steam stripper 120. Process conditions may be adjusted in steam stripper 120 to maximize the concentration and removal of methanol, other similarly volatile compounds, and other compounds solubilized in methanol present in condensate $FC_2$.

Volatiles in condensate $FC_2$ are concentrated as they rise through steam stripper 120. A vapour phase $V_1$ at the top of steam stripper 120, typically comprising about 40 wt. % to about 60 wt. % methanol of vapour $V_1$, is removed from the top of steam stripper 120 and directed to a partial condenser 130. Vapour phase $V_1$ contains some water vapour and most of the volatiles present in condensate $FC_2$. In some embodiments, partial condenser 130 comprises a segregated section of an evaporator effect of the Kraft pulping process. Heat generated via condensation in steam stripper 120 promotes evaporation of the black liquor in the evaporator effect. Partial condenser 130 produces a condensed liquid stream called a reflux $R_1$ which is returned to the top of steam stripper 120 for further concentration of volatiles.

A vapour phase $V_2$ from partial condenser 130 is directed to a rectifier column 140 to remove remaining volatile compounds. A condensate $FC_3$ produced by rectifier column 140 is directed to a decanter 150. A decanted phase $FC_4$ comprising water, methanol, and a variety of contaminants (e.g. ethanol, etc.) may be returned to steam stripper 120.

A vapour phase $V_3$ at the top of rectifier column 140 is directed from the top of the column to a partial condenser 160. Partial condenser 160 produces a reflux $R_2$ which is returned to the top of rectifier column 140 to remove remaining volatile compounds (e.g. ethanol, etc.). A vapour phase $V_4$ from partial condenser 160 is directed to a total condenser 170 where a concentrated liquid comprising methanol, water, and some residual volatile compounds is produced. Residual volatile compounds (such as ketones, ammonia, etc.) are removed from a top of total condenser 170 and directed to the Kraft mill's CNCG stream which is burned in the recovery boiler, in the lime kiln or in a dedicated incinerator. Where foul condensate FC is treated with acid $S_1$, as described elsewhere herein, the CNCG stream is sufficiently free of ammonia. Accordingly FCTP 100 reduces NOx emissions from the Kraft mill.

Total condenser 170 produces a purified reflux $R_3$ comprising greater than about 80 wt. % methanol which is directed to methanol storage tank 180. In some embodiments, $R_3$ is greater than about 90 wt. % methanol. Since most volatile compounds are removed from foul condensate FC by air stripper 110, the methanol produced by FCTP 100 can be of sufficient purity to be used as merchant methanol in Kraft pulping processes. In some embodiments, the purified methanol may be further treated by reverse osmosis and/or with activated carbon. The activated carbon may act as an adsorbent surface for materials that are sparingly soluble in the methanol. In some embodiments, purified methanol from storage tank 180 is directed to the Kraft mill's CNCG stream to reduce the pressure inside tank 180.

Removal of volatile compounds by air stripper 110 prior to stripping the methanol from foul condensate FC produces a stripped condensate $FC_5$ suitable (i.e. sufficiently free of volatile compounds) for use in Kraft pulping (i.e. a bleach plant) to displace fresh water.

Acidification of foul condensate FC reduces NOx emissions by converting ammonia to non-volatile ammonium ions. The methanol stripped from foul condensate FC by steam stripper 120 may be distilled and/or treated by reverse osmosis and/or activated carbon to further purify and/or polish the methanol. Thus, FCTP 100 yields a stripped condensate $FC_5$ with minimal volatile contaminants for re-use in the Kraft pulping process while minimizing NOx formation and producing methanol with minimal contaminants that can be used as a substitute for merchant methanol in Kraft pulping processes.

Figure 3:
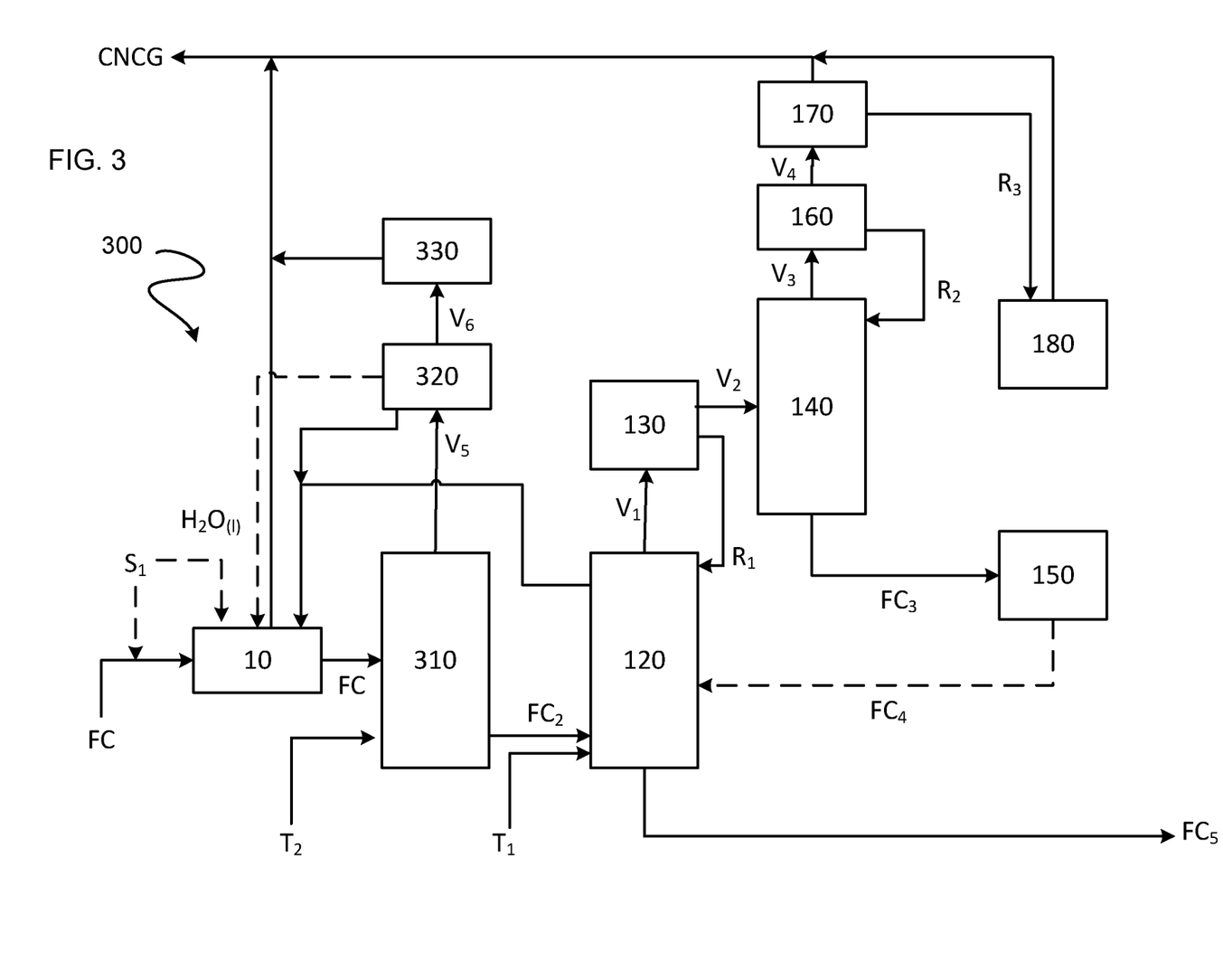
FIG. 3 is a schematic illustration of a foul condensate treatment process according to an example embodiment of the present invention.

In some embodiments, volatile compounds are removed by successive steam stripping. A FCTP 300 in accordance with an example embodiment is illustrated in FIG. 3. Many features and components of FCTP 300 are similar to features and components of FCTP 100, with the same reference numerals being used to indicate features and components that are similar between the embodiments. FCTP 300 comprises a steam stripper 310 for removing volatile compounds. FC stored in a feed tank 10 is supplied to steam stripper 310. In some embodiments, the FC is heated before introduction into steam stripper 310. Steam stripper 310 is a device that brings foul condensate FC into contact with a flow of steam into which volatile compounds are scrubbed. In some embodiments, steam stripper 310 comprises a packed column, a tray column, a fluidized-bed column, or a froth column. In some embodiments, steam stripper 310 comprises a packed tower such as a mass transfer column. The column may have structured, fixed, or loose packing as is conventionally known. Steam stripper 310 is provided with multiple vapour and/or liquid equilibrium stages using trays and/or continuous packing at a mid-point in the column. Steam $T_2$ is introduced into the bottom of steam stripper 310 to vaporize volatile compounds present in foul condensate FC. In some embodiments, steam $T_2$ comprises steam from a boiler and/or from one or more of the evaporator effects of the Kraft pulping. In some embodiments, steam $T_2$ may be produced in a re-boiler installed at a bottom end of steam stripper 310.

Steam stripper 310 maintains the temperature of foul condensate FC below about 100° C. In some embodiments, steam stripper 310 maintains the temperature of foul condensate FC less than about 100° C. In some embodiments, steam stripper 310 maintains the temperature of foul condensate FC less than about 90° C.

In some embodiments, the mass of steam $T_1$ used to strip foul condensate FC is less than about 10 wt. % of the mass of the foul condensate FC supplied to steam stripper 310. In some embodiments, the mass of steam $T_1$ is less than about 5 wt. % of the mass of the foul condensate FC supplied to steam stripper 310. Process conditions may be adjusted in steam stripper 310 to maximize the concentration and removal of volatile compounds.

Volatiles in foul condensate FC are concentrated as they rise through steam stripper 310. A vapour phase $V_5$ at the top of steam stripper 310 is directed to a total condenser 320 for removing water from vapour phase $V_5$. Condensed water vapour $H_2O_{(l)}$ is directed to feed tank 10. A vapour phase $V_6$ is directed from total condenser 320 to the Kraft mill's CNCG stream via a steam ejector 330.

If NOx control is required, acid $S_1$ may be added to foul condensate FC to convert ammonia to non-volatile ammonium ions. The ammonium ions exit steam stripper 310 with the resulting concentrate $FC_2$. In the example embodiment illustrated in FIG. 3, acid $S_1$ is added to foul condensate FC prior to its introduction into steam stripper 310. For example, acid $S_1$ may be added to feed tank 10 or to foul condensate FC prior to storage in feed tank 10. In some embodiments, acid $S_1$ comprises sulphuric acid and/or sodium bisulphite. The ammonium ion associates with sulphate anions in solution. Other organic and/or inorganic acids and/or acid salts may be used to convert ammonia to ammonium ions.

In some other embodiments, ammonia is scrubbed from the overhead gas of steam stripper 310 using acid $S_1$. Recovered ammonium ions are directed to effluent treatment. For example, in the example embodiment illustrated in FIG. 4, a FCTP 400 is schematically illustrated. FCTP 400 comprises a stripper 410 for removing ammonia and volatile compounds. Many features and components of FCTP 400 are similar to features and components of FCTP 100 and FCTP 300, with the same reference numerals being used to indicate features and components that are similar between the embodiments. Stripper 410 comprises steam stripper 310 and an ammonia scrubber 412 for scrubbing ammonia from overhead gas using acid $S_1$. Recovered ammonium $NH_4^+$ is directed to Kraft mill effluent treatment where ammonium is beneficial as a nutrient in biological treatment. In some embodiments, ammonia is recovered as ammonium sulphate $((NH_4)_2SO_{4(l)})$, which is directed to Kraft mill effluent treatment where ammonium is beneficial as a nutrient in biological treatment. In the illustrated embodiment, stripper 410 forms a single device comprising steam stripper 310 and ammonia scrubber 412. Persons skilled in the art will recognize that steam stripper 310 and ammonia scrubber 412 may be separate devices. A vapour phase $V_7$ is directed from stripper 410 to the Kraft mill's CNCG stream via a steam ejector 330.

Figure 4:
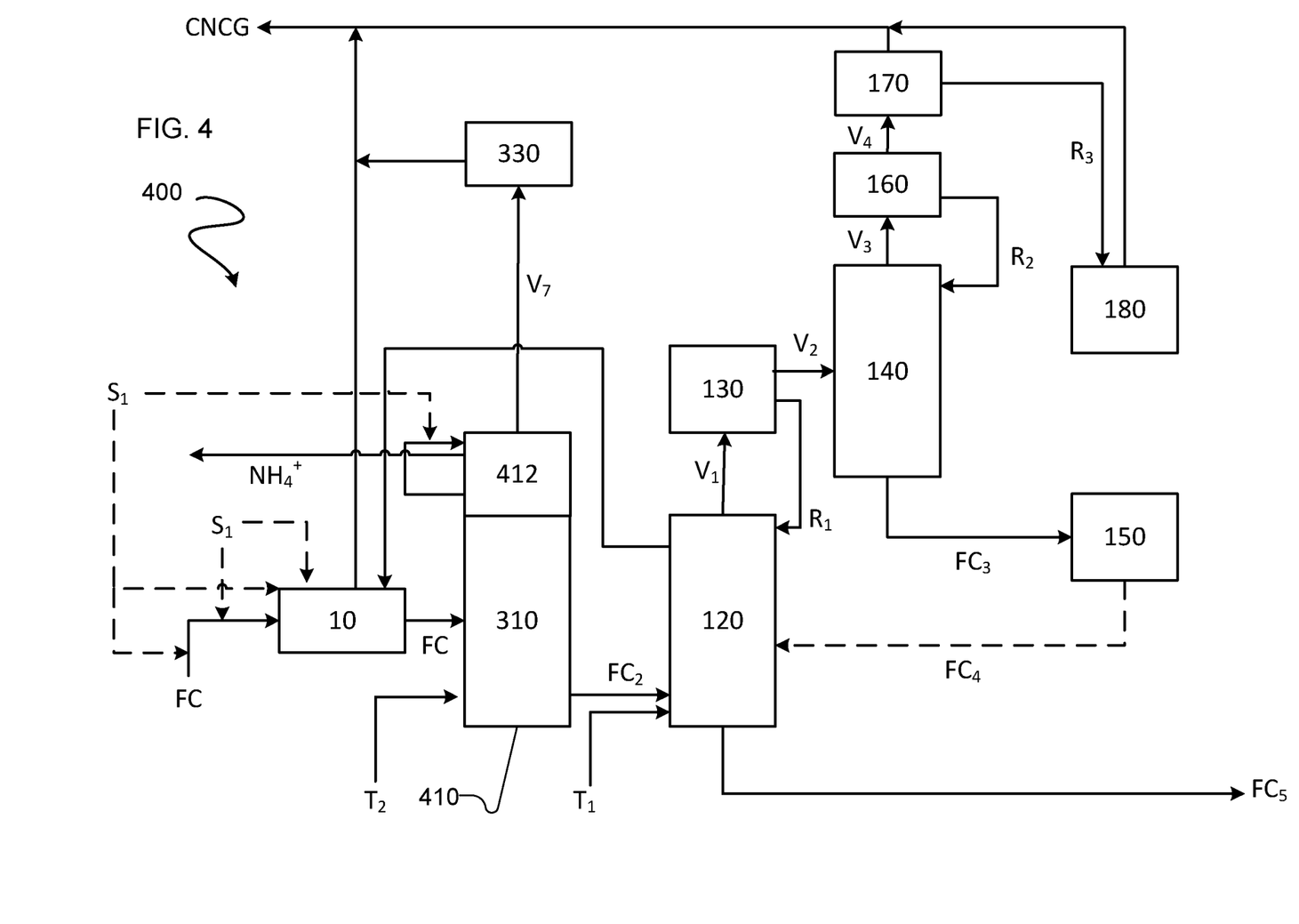
FIG. 4 is a schematic illustration of a foul condensate treatment process according to an example embodiment of the present invention.

Since higher temperatures and/or a higher gas/liquid ratio is required to remove methanol from foul condensate FC, steam stripper 310 effectively removes volatile compounds while retaining a large percentage of the methanol in the resulting condensate $FC_2$. Methanol is subsequently concentrated and purified by FCTP 300 in a second separation stage (e.g. steam stripper 120). Following treatment in steam stripper 310, the concentration of volatile compounds in condensate $FC_2$ is reduced. Accordingly, the volatile compounds are not available to in such high concentrations to interact to form less volatile contaminants that are more difficult to separate from foul condensate FC. In some embodiments, the volatile compounds are not available in such high concentrations to complicate methanol purification by solubilizing in steam stripper 310 to form distillation azeotropes. The methanol produced by FCTP 300 and 400 thus has minimal contaminants and may be used as a substitute for merchant methanol in Kraft pulping processes.

Persons skilled in the art will recognize that the FCTPs described herein may optionally include any of a number of ancillary operations not shown. Some of these operations may be performed to improve chemical equilibrium conditions and/or chemical reaction kinetics, and/or contaminant removal efficiency. These operations may include one or more of the following: cooling, reheating, compressing, and expanding. For example, heat exchangers may be used to cool and/or heat the condensate stream to desired temperatures to improve contaminant removal efficiencies.

Persons skilled in the art will also recognize that the FCTPs described herein may further comprise a control unit to perform various system- and component-level control functions. The control unit, together with instrumentation and signal lines, is not shown for simplicity.

Some advantages of the FCTPs described herein include one or more of:
(i) A stripped condensate with minimal volatile compounds for re-use in the Kraft pulping process is produced.
(ii) NOx formation is minimized or eliminated.
(iii) Methanol having minimal contaminants and that can be used as a substitute for merchant methanol in Kraft pulping processes is produced.

NON-LIMITING EXAMPLES

Non-limiting example applications of the invention are given below. Persons skilled in the art will recognize that these examples may be modified to suit the needs of a specific application in which the foul condensate entering the system is substantially free of a specific contaminant (e.g. methanol, sulphur-containing compounds, ethanol, etc.), in which case its removal is not needed. Moreover, in some cases, it may be desirable to forego the removal of a specific contaminant due to other constraints specific to the application. For example, the system can be tailored to remove methanol and volatile compounds and other similarly volatile compounds only.

Example 1—One Stage Steam Stripping

The following examples are simulated treatments of a foul condensate (FC) using a HYSYS thermodynamic modelling program. A foul condensate having a temperature of 85° C. was steam stripped in a steam stripping column (e.g. steam stripper 120). The stripping column was equipped with 20 vertical trays and foul condensate FC was introduced into the stripping column at tray 5. Overhead vapours were removed from the stripping column and directed to a rectifier column (e.g. rectifier column 140) via a partial condenser (e.g. partial condenser 130). The rectifier column was equipped with 15 vertical trays and the overhead vapours were directed into the rectifier column at tray 6. Vapours were removed from the rectifier column and directed to a total condenser (e.g. total condenser 170) via a partial condenser (e.g. partial condenser 160). Vapours from the total condenser were directed to a CNCG system ("CNCG 2"). Condensed methanol from the total condenser is directed to storage (e.g. storage tank 180). The condensate (e.g. condensate $FC_3$) at the bottom of the rectifier column was directed to effluent treatment in Kraft pulping. The compositions of the various liquid and vapour phases as a measure of flow rate are shown in Table 2.

TABLE 2

| Flow kg/hr | Foul Condensate (FC) | Rectifier Feed | Stripped Condensate | Rectifier Bottom | To CNCG 2 | Pure MeOH |
|---|---|---|---|---|---|---|
| Methanol | 3610 | 3595 | 13.6 | 147 | 103 | 3345 |
| Water | 321343 | 1517 | 319761 | 1508 | 0.1 | 9 |
| Total reduced sulphur (TRS) | 553 | 502 | 50.9 | 1.5 | 244 | 256 |
| Ammonia | 130 | 130 | 0 | 0 | 72.5 | 57.6 |
| Other organics | 276 | 276 | 0 | 179 | 30.2 | 67.2 |
| Total | 325911 | 6021 | 319826 | 1835 | 450 | 3735 |

Example 2—Pre-Treatment Air Stripping and Second Stage Steam Stripping

The one stage steam stripping treatment process of Example 1 was preceded by an air stripping stage. A foul condensate having a temperature of 55° C. was air stripped in an air stripping column (e.g. air stripper 110). The stripping column was equipped with 10 vertical trays. Vapours from the air stripping column were directed to a DNCG system. Resulting condensate (e.g. condensate $FC_2$) was directed from the bottom of the air stripping column to a second stage steam stripper (i.e. the steam stripping column of Example 1). The compositions of the various liquid and vapour phases as a measure of flow rate are shown in Table 3.

TABLE 3

| Flow kg/hr | Foul Condensate (FC) | To DNCG | Air Stripper Feed | Stripped Condensate | Rectifier Bottom | To CNCG 2 | Pure MeOH |
|---|---|---|---|---|---|---|---|
| Methanol | 3610 | 478 | 3132 | 10 | 560 | 280 | 2282 |
| Water | 321343 | 4077 | 317265 | 316126 | 1131 | 0 | 8 |
| Total reduced sulphur (RS) | 553 | 469 | 84 | 48 | 2 | 18 | 16 |
| Ammonia | 130 | 129 | 1 | 0 | 0 | 1 | 0 |
| Other organics | 276 | 136 | 141 | 0 | 121 | 2 | 18 |
| Air | 0 | 32438 | 152 | 0 | 0 | 152 | 0.1 |
| Total | 325911 | 5289 | 320623 | 316183 | 1815 | 302 | 2323 |

By removing volatile compounds in the air stripping column prior to removing methanol via second stage steam stripping, lower concentrations of the volatile compounds were present to mix with methanol in the steam stripping column. Accordingly, a higher purity methanol and a higher purity stripped condensate were observed. The composition of the DNCG stream was calculated to be below its Lower Explosion Limit (LEL). Traces of reduced sulfur compounds remaining in the stripped condensate from the two stage air and steam stripping process were oxidized to non-odorous forms, thereby improving the stripped condensate quality.

Example 3—Pre-Treatment Steam Stripping and Second Stage Steam Stripping

The one stage steam stripping treatment process of Example 1 was preceded by a pre-treatment steam stripping stage. A foul condensate having a temperature of 85° C. was steam stripped in a steam stripping column (e.g. steam stripper 310). The stripping column was equipped with 10 vertical trays. Vapours from the steam stripping were directed to a CNCG system ("CNCG 1"). Resulting condensate (e.g. condensate $FC_2$) was directed from the bottom of the steam stripping column to a second stage steam stripper (i.e. the steam stripping column of Example 1). The compositions of the various liquid and vapour phases as a measure of flow rate are shown in Table 4.

TABLE 4

| Flow kg/hr | Foul Condensate (FC) | To CNCG 1 | Pre-Treatment Steam Stripper Feed | Stripped Condensate | Rectifier Bottom | To CNCG 2 | Pure MeOH |
|---|---|---|---|---|---|---|---|
| Methanol | 3610 | 412 | 3197 | 10 | 645 | 442 | 2101 |
| Water | 321343 | 4175 | 335091 | 334034 | 1049 | 1 | 8 |
| Total reduced sulphur (TRS) | 553 | 483 | 70 | 49 | 3 | 8 | 10 |
| Ammonia | 130 | 130 | 0 | 0 | 0 | 0 | 0 |
| Other organics | 276 | 141 | 135 | 0 | 119 | 2 | 15 |
| Total | 325911 | 5342 | 338494 | 334093 | 1814 | 454 | 2133 |

By removing volatile compounds in the pre-treatment steam stripping column prior to removing methanol via second stage steam stripping, lower concentrations of the volatile compounds were present to mix with methanol in the second stage steam stripping column. Accordingly, a higher purity methanol and a higher purity stripped condensate were observed.

INTERPRETATION OF TERMS

Unless the context clearly requires otherwise, throughout the description and the claims:
  "comprise", "comprising", and the like are to be construed in an inclusive sense, as opposed to an exclusive or exhaustive sense; that is to say, in the sense of "including, but not limited to";
  "connected", "coupled", or any variant thereof, means any connection or coupling, either direct or indirect, between two or more elements; the coupling or connection between the elements can be physical, logical, or a combination thereof; elements which are integrally formed may be considered to be connected or coupled;
  "herein", "above", "below", and words of similar import, when used to describe this specification, shall refer to this specification as a whole, and not to any particular portions of this specification;
  "or", in reference to a list of two or more items, covers all of the following interpretations of the word: any of the items in the list, all of the items in the list, and any combination of the items in the list;
  the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

While a number of exemplary aspects and embodiments are discussed herein, those of skill in the art will recognize certain modifications, permutations, additions and sub-combinations thereof.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A foul condensate treatment process comprising:
(a) removing volatile compounds from foul condensate by an air stripper to produce a resulting condensate;
(b) maintaining the temperature of the foul condensate in the air stripper between about 50° C. and about 60° C.; and
(c) removing methanol from the resulting condensate.

2. A foul condensate treatment process comprising:
(a) removing volatile compounds from foul condensate by an air stripper to produce a resulting condensate, wherein a mass of oxygen-containing gas is used to strip the foul condensate in the air stripper and the mass of oxygen-containing gas is controlled to maintain the oxygen-containing gas below its Lower Explosive Limit (LEL); and
(b) removing methanol from the resulting condensate.

3. The process according to claim 2, wherein the mass of oxygen-containing gas is less than about 10% by weight (wt. %) of the mass of the foul condensate supplied to the air stripper.

4. A foul condensate treatment process comprising:
(a) removing volatile compounds from foul condensate by an air stripper to produce a resulting condensate, wherein a mass of oxygen-containing gas is used to strip the foul condensate in the air stripper and the mass of oxygen-containing gas is less than about 10% by weight (wt. %) of the mass of the foul condensate supplied to the air stripper; and
(b) removing methanol from the resulting condensate.

5. A foul condensate treatment process comprising:
(a) removing volatile compounds from foul condensate by a first steam stripper to produce a resulting condensate;
(b) maintaining the temperature of the foul condensate below about 100° C. in the first steam stripper; and
(c) removing methanol from the resulting condensate.

6. A foul condensate treatment process comprising:
(a) removing volatile compounds from foul condensate by a first steam stripper to produce a resulting condensate, wherein a mass of steam used to strip the foul condensate in the first steam stripper is less than about 10% by weight (wt. %) of the mass of the foul condensate supplied to the first steam stripper; and
(b) removing methanol from the resulting condensate.

7. A foul condensate treatment process comprising:
(a) removing volatile compounds from foul condensate to produce a resulting condensate;
(b) maintaining the temperature of the resulting condensate above about 100° C. in the second steam stripper; and
(c) removing methanol from the resulting condensate by a second steam stripper.

8. A foul condensate treatment process comprising:
(a) removing volatile compounds from foul condensate to produce a resulting condensate;
(b) removing methanol from the resulting condensate by a second steam stripper; and
(c) maintaining the temperature of the resulting condensate between about 100° C. and about 120° C. in the second steam stripper.

9. A foul condensate treatment process comprising:
(a) removing volatile compounds from foul condensate to produce a resulting condensate, and
(b) removing methanol from the resulting condensate by a second steam stripper, wherein a mass of steam used to strip the resulting condensate in the second steam stripper is greater than about 10% by weight (wt. %) of the mass of the foul condensate supplied to the second steam stripper.

* * * * *